United States Patent
Bouvet et al.

(10) Patent No.: US 8,450,725 B2
(45) Date of Patent: May 28, 2013

(54) SEMICONDUCTOR TRANDUCER AND ITS USE IN A SENSOR FOR DETECTING ELECTRON-DONOR OR ELECTRON-ACCEPTOR SPECIES

(75) Inventors: Marcel Bouvet, La Rochette (FR); Vicente Parra, Valladolid (ES)

(73) Assignees: Universite Pierre et Marie Curie, Paris (FR); Centre National de la Recherche, Paris (FR)

( * ) Notice: Subject to any disclaimer, the term of this patent is extended or adjusted under 35 U.S.C. 154(b) by 510 days.

(21) Appl. No.: 12/682,128

(22) PCT Filed: Sep. 24, 2008

(86) PCT No.: PCT/FR2008/001325
§ 371 (c)(1),
(2), (4) Date: Apr. 8, 2010

(87) PCT Pub. No.: WO2009/071774
PCT Pub. Date: Jun. 11, 2009

(65) Prior Publication Data
US 2010/0218593 A1 Sep. 2, 2010

(30) Foreign Application Priority Data
Oct. 15, 2007 (FR) .................................... 07 07209

(51) Int. Cl.
*H01L 21/3205* (2006.01)
(52) U.S. Cl.
USPC ................. 257/40; 257/414; 438/99; 73/23.2
(58) Field of Classification Search
USPC .............. 257/40, 414; 438/99; 73/23.2–31.07
See application file for complete search history.

(56) References Cited

U.S. PATENT DOCUMENTS

| | | | |
|---|---|---|---|
| 5,500,537 A * | 3/1996 | Tsumura et al. | 257/40 |
| 6,278,127 B1 * | 8/2001 | Dodabalapur et al. | 257/40 |
| 6,484,559 B2 * | 11/2002 | Dodabalapur et al. | 73/23.34 |

FOREIGN PATENT DOCUMENTS

| | | |
|---|---|---|
| EP | 1085319 | 3/2001 |
| WO | WO 9600383 A1 * | 1/1996 |
| WO | 0191202 | 11/2001 |

OTHER PUBLICATIONS

Clarisse et al., "Field-effect transistor with diphthalocyanine thin film," Electronics Letters, vol. 24, No. 11, pp. 674-675, May 26, 1988.*
Clarisse et al., "The operation and characteristics of diphthalocyanine field effect transistors" J. Appl. Phys. 69, 3324 (1991); http://dx.doi.org/10.1063/1.348555.*

(Continued)

*Primary Examiner* — Cheung Lee
*Assistant Examiner* — Christopher Johnson
(74) *Attorney, Agent, or Firm* — Sofer & Haroun, LLP (57) ABSTRACT

The invention relates to a semi-conductor transducer, and to the use thereof in an electron donor or electron acceptor space sensor. Said transducer consists of an insulating substrate on the surface of which two electrodes and a semiconductor sensitive element are provided. The sensitive element consists of a layer of a semiconductor molecular material M1 having a conductivity $C_1$ and a layer of a semiconductor molecular material M2 having a conductivity C2 and a forbidden bandwidth $E_{g2} < 1$ eV. The material layer M1 is in contact with the electrodes. The material layer M2 is deposited on the material layer M1 and is not in contact with the electrodes. The conductivities are such that $C_2/C_1 \geq 1$.

16 Claims, 6 Drawing Sheets

OTHER PUBLICATIONS

Passard, et al., "Gaseous oxidation and compensating reduction of lutetium bis-phthalocyanine and lutetium phthalo-naphthalocyanine films," Thin Solid Films, vol. 271, 1, Dec. 15, 1995, pp. 8-14(7); http://dx.doi.org/10.1016/0040-6090(95)06673-X.*

Germain et al., "Influence of peripheral electron-withdrawing substituents on the conductivity of zinc phthalocyanine in the presence of gases. Part 2: oxidizing gases," Thin Solid Films, vol. 333, Issues 1-2, Nov. 25, 1998, pp. 235-239, ISSN 0040-6090, 10.1016/50040-6090(98)00830-X.*

* cited by examiner

SEMICONDUCTOR TRANDUCER AND ITS USE IN A SENSOR FOR DETECTING ELECTRON-DONOR OR ELECTRON-ACCEPTOR SPECIES

RELATED APPLICATIONS

This application is a National Phase application of PCT/FR2008/001325, filed on Sep. 24, 2008, which in turn claims the benefit of priority from French Patent Application No. 07 07209, filed on Oct. 15, 2007, the entirety of which are incorporated herein by reference

BACKGROUND

1. Field of the Invention

The present invention relates to a semiconductor transducer and to its use in a sensor for detecting electron-donor or electron-acceptor species.

2. Description of Related Art

Various devices for detecting gaseous molecules, especially those comprising a semiconductor transducer of the resistor, transistor or diode type, are known.

There are many types of diodes having various types of semiconductor materials, a few examples of which have been used as chemical sensors. In particular, R. Dobulans, J. Latvels, I. Muzikante, E. Fonavs, A. Tokmakov and M. Bouvet ["*Molecular diode for gas sensing*", Proceedings of the NENAMAT Mobilization Workshop "Nanomaterials and Nanotechnologies", 30-31 March, Riga, 2005, 130] discloses a diode in which the two semiconductor layers are formed by two different molecular materials, of type p and type n respectively. However, the geometry and the operation of this device are not optimized for its use as a chemical sensor, and its forming operation is complex.

M. Bouvet and A. Pauly [Encyclopedia of Sensors, Editors C. A. Grimes, E. C. Dickey and M. V. Pishko, Vol. 6, pp. 227-269] describe transducers of the resistor type or of the field-effect transistor type, in which the sensitive element is an electroactive molecular material. Such materials are described in particular by J. Simon, J.-J. André and A. Skoulios ["*Molecular Materials. I: Generalities*", Nouv. J. Chim., 1986, 10, 295-311] and by J. Simon and P. Bassoul ["*Design of Molecular Materials*", Wiley, Chichester, 2000].

A field-effect transistor is formed by the following succession of layers: a conducting substrate (for example doped Si); an insulating layer (for example $SiO_2$ or $Si_3N_4$); and a layer of a metal monophthalocyanine (MPc). The MPc layer is connected to a source electrode and to a drain electrode, and the conducting substrate is connected to a gate electrode. The MPc layer constitutes both the sensitive layer and the material in which the measured current flows, said current being modulated by the voltage applied to the gate electrode. The molecular material may be a semiconductor polymer, phthalocyanine (substituted or unsubstituted), a porphyrin (substituted or unsubstituted), an oligothiophene (substituted or unsubstituted), a pentacene, a fullerene or a perylene derivative. Such a device performs well for detecting molecules. However, its production involves complicated technological steps.

A gas detector of the resistor type comprises, for example, an alumina substrate on one of the faces of which two interdigitated Pt electrodes are placed, on the top of which a film of copper phthalocyanine (CuPc) is deposited. The other face of the substrate comprises Pt resistors for heating the substrate. The conductivity of the CuPc increases with the $O_3$ content or $NO_2$ content of a gas mixture with which the CuPc is in contact. The drawback of such a device lies firstly in the absence of selectivity relative to the gas molecules to be detected, and secondly its performance limitation.

OBJECTS AND SUMMARY

Surprisingly, the inventors have found that the deposition, on the sensitive surface of a semiconductor resistor, of a film of a different semiconductor material chosen according to well-defined criteria makes the transducer selective with respect to molecules to be detected and substantially improves its performance as a sensor, by creating a particular heterojunction.

The object of the present invention is to provide a sensor for detecting electron-donor or electron-acceptor species which performs in a manner which is novel and better than the sensors of the prior art. This sensor operates at room temperature, unlike a number of prior sensors.

The subjects of the present invention are a semiconductor transducer and a sensor for detecting electron-donor or electron-acceptor species that contain such a transducer.

A transducer according to the present invention is formed by an insulating substrate on the surface of which two electrodes and a semiconductor sensitive element are deposited, characterized in that:

the sensitive element is formed by a layer of a semiconductor molecular material M1 which has a conductivity $C_1$ and a layer of a semiconductor molecular material M2 which has a conductivity $C_2$ and a bandgap $E_{g2}<1$ eV;

the layer of material M1 is in contact with the electrodes;

the layer of material M2 is deposited on the layer of material M1 and is not in contact with the electrodes;

the conductivities are such that $C_2/C_1 \geqq 1$; and the material M1 is: a monophthalocyanine $M^{II}Pc$ of a metal M in oxidation state II chosen from Fe, Co, Ni, Cu, Zn, Pt and Pd; a monophthalocyanine $M^{III}Pc$ of a metal M in oxidation state III in the form GaOH, GaCl, InCl, AlCl, AlF or AlOH; a monophthalocyanine $M^{IV}Pc$ of a metal M in an oxidation state IV in the form $Si(OH)_2$, $SiCl_2$, $SnCl_2$, TiO or VO; a polyphthalocyanine, the repeat unit of which is MPc, the metal M being in the form SiO, SnO, GeO, FePyrazine, RuPyrazine, AlF or GaF; an organic compound chosen from oligothiophenes, whether substituted or not, tetracenes, pentacenes, fullerenes, tetracarboxylic naphthalenes, naphthalene dianhydrides, naphthalene diimides, tetracarboxylic perylenes, perylene dianhydrides, perylene diimides, triarylamines, triphenylenes and tetracyanoquinodimethanes; or a semiconductor polymer chosen from polythiophenes and polyparaphenylenevinylenes.

The thickness of the layer of material M1 and the thickness of the layer of material M2 are between 2 and 1000 nm, preferably between 20 nm and 100 nm. The thickness of the electrodes is between 2 nm and 1000 nm.

DETAILED DESCRIPTION

Figure 1:
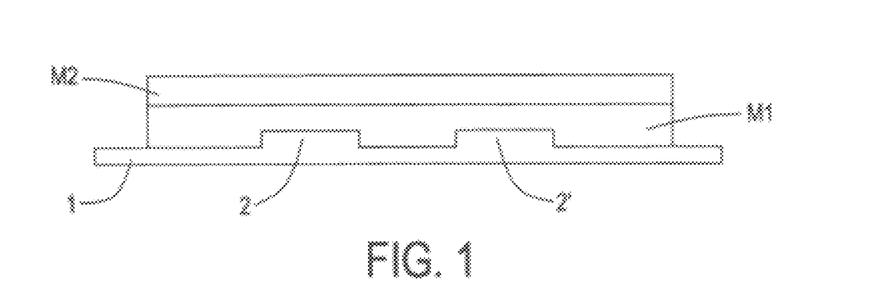
FIG. 1 shows a schematic view of a transducer according to the invention.

FIG. 1 shows a schematic view of a transducer according to the invention. The substrate is denoted by the reference 1, the electrodes by the references 2 and 2' and the layers of material M1 and M2 by the references M1 and M2 respectively.

The material M2, which has a bandgap $E_{g2}<1$ eV, is preferably chosen from metal bisphthalocyanines ($M'Pc_2$), metal bisporphyrins ($M'Por_2$) and metal bisnaphthalocyanines ($M'Nc_2$) and from similar metal compounds derived from a tetrapyrazinoporphyrazine, a thiophenoporphyrazine, a tetraarenoporphyrazine, a tetrapyridoporphyrazine, an anthracocyanine, a triphenylocyanine or a phenanthrocyanine, in which M'=U, Zr, Y or Ln (Ln being La, Ce, Pr, Nd, Sm, Eu, Gd, Tb, Dy, Ho, Er, Tm, Yb or Lu). The material M2 may furthermore be chosen from metal trisphthalocyanines ($M'_2Pc_3$), metal trisporphyrins ($M'_2Por_3$), metal trisnaphthalocyanines ($M'_2Nc_3$) and from similar metal compounds derived from a tetrapyrazinoporphyrazine, a thiophenoporphyrazine, a tetraarenoporphyrazine, a tetrapyridoporphyrazine, an anthracocyanine, a triphenylocyanine or a phenanthrocyanine, in which M' is Y or Ln).

As particular examples of material M2, mention may be made of radical lanthanide bisphthalocyanines $LnPc_2$ (Ln being La, Pr, Nd, Sm, Eu, Gd, Tb, Dy, Ho, Er, Tm, Yb or Lu). The compound $LuPc_2$ satisfying the following formula is particularly preferred:

The bisphthalocyanines are prepared by a method consisting in reacting ortho-dicyanobenzene with a lanthanide salt, either in solution in an alcohol in the presence of a strong organic base, or without a solvent, according to the operating methods described in particular by: I. S. Kirin et al. [Russ. J. Inorg. Chem. 1965, 10, 1065-1066]; I. S. Kirin et al. [Russ. J. Inorg. Chem. 1967, 12, 369-372]; C. Clarisse et al. [Inorg. Chim. Acta 1987, 130, 139-144]; and A. De Cian et al. [Inorg. Chem. 1985, 24, 3162-3167].

Among monophthalocyanines $M^{II}Pc$ that can be used as material M1, the monophthalocyanines $M^{II}Pc$ in which M is copper, nickel or zinc are particularly advantageous. The monophthalocyanine may optionally bear substituents, especially halogens such as F, Cl or Br, F being particularly preferred. Among fluorinated monophthalocyanines, mention may be made in particular of those having 4, 8 or 16 F atoms, satisfying the following formulae:

F4PcCu

-continued

F8PcCu

F16PcCu

The degree of fluorination of a monophthalocyanine has little impact on the bandgap $E_g$ but promotes stabilization of the empty electron levels and full electron levels (highest occupied molecular orbitals and lowest unoccupied molecular orbitals) with a quasicontinuous shift from $CuF_0Pc$ to $CuF_{16}Pc$ of 3.16 to 4.46 eV for electron affinities of 5.20 to 6.39 eV in respect of ionization potentials (cf. R. Murdey, N. Sato and M. Bouvet, Mol. Cryst. Liq. Cryst., 2006, 455, 211-218) relative to the vacuum level. As a result, a compound $M^{II}Pc$ in which the monophthalocyanine is nonfluorinated has p-type semiconductor properties, whereas a compound $M^{II}Pc$ in which the monophthalocyanine is perfluorinated i.e. $F_{16}Pc$, has n-type semiconductor properties. The compound $M^{II}F_8Pc$ has intermediate properties and its behavior depends in particular on the electrodes forming part of the transducer.

Copper monophthalocyanines CuPc, zinc monophthalocyanine ZnPc and nickel monophthalocyanine NiPc are commercial products, supplied in particular by the company Sigma-Aldrich.

A Cu, Zn or Ni monophthalocyanine having 16 F atoms may be prepared by reacting tetrafluoro-1,2-dicyanobenzene with the metal or the metal salt according to the operating method described by J. M. Birchall et al. [J. Chem. Soc., 1970, 2667] or by D. D. Eley, et al. [J. Chem. Soc., Faraday Trans., 1973, 69 1808]. Perfluorinated Cu or Zn monophthalocyanines are commercial products supplied by the company Sigma-Aldrich.

A Cu monophthalocyanine having 8 F atoms may be prepared by reacting 4,5-difluoro-1,2-dibromobenzene with an excess of copper cyanide CuCN in an organic solvent, for example DMF, and then by treating the reaction mixture with a concentrated aqueous ammonia solution.

A Cu monophthalocyanine having 4 F atoms is a product supplied by the company Synthec GmbH.

Among perylene diimides that can be used as material M2, mention may in particular be made of N,N-dipentyl-perylene tetracarboxylic acid diimide.

Among oligothiophenes that can be used as material M2, mention may in particular be made of α,ω-dihexyl sexithiophene.

The insulating substrate bearing the electrodes, the layer of material M1 and the layer of material M2 may be formed by an intrinsic insulating material, such as alumina or glass, or by a material coated with a dielectric (for example silicon coated with a film of silica or silicon nitride).

Figure 2:
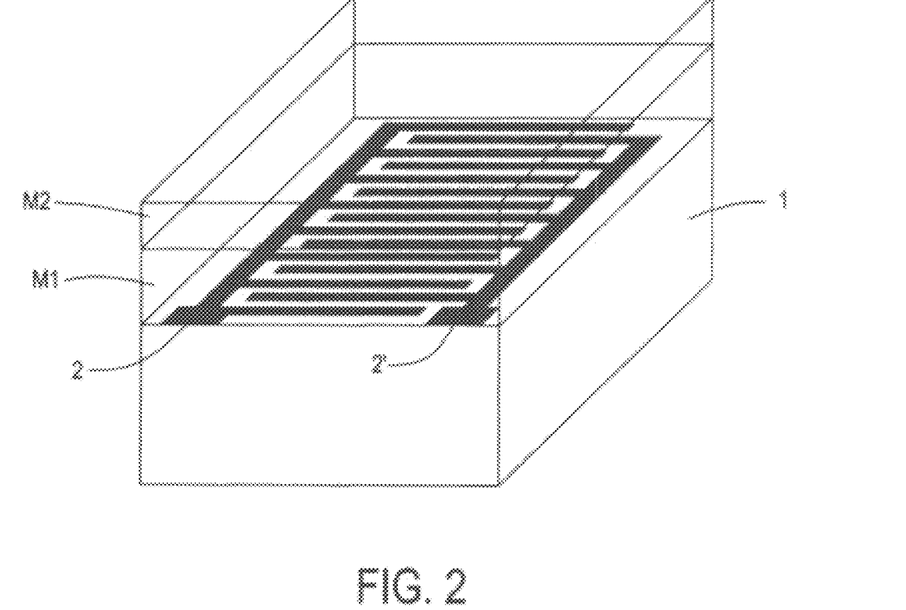
FIG. 2 shows interdigitated electrodes according to the invention.

The electrodes are formed for example by a film of gold or a film of indium tin oxide (ITO). They are preferably in the form of interdigitated electrodes, as shown in particular in FIG. 2. The electrodes are deposited on the insulating substrate by conventional processes, for example by vacuum thermal evaporation or by lithographic techniques.

A transducer according to the invention may be produced by a process consisting in depositing electrodes on an insulating substrate, followed by the layer of material M1 and then the layer of material M2.

An Au electrode may be deposited by thermal evaporation.
An ITO electrode may be deposited by vacuum sputtering.
The film of material M1 may be deposited by vacuumed sublimation, by spin coating or by solvent casting.
The film of material M2 may be deposited by vacuum sublimation, by spin coating or by solvent casting.

Figure 3:
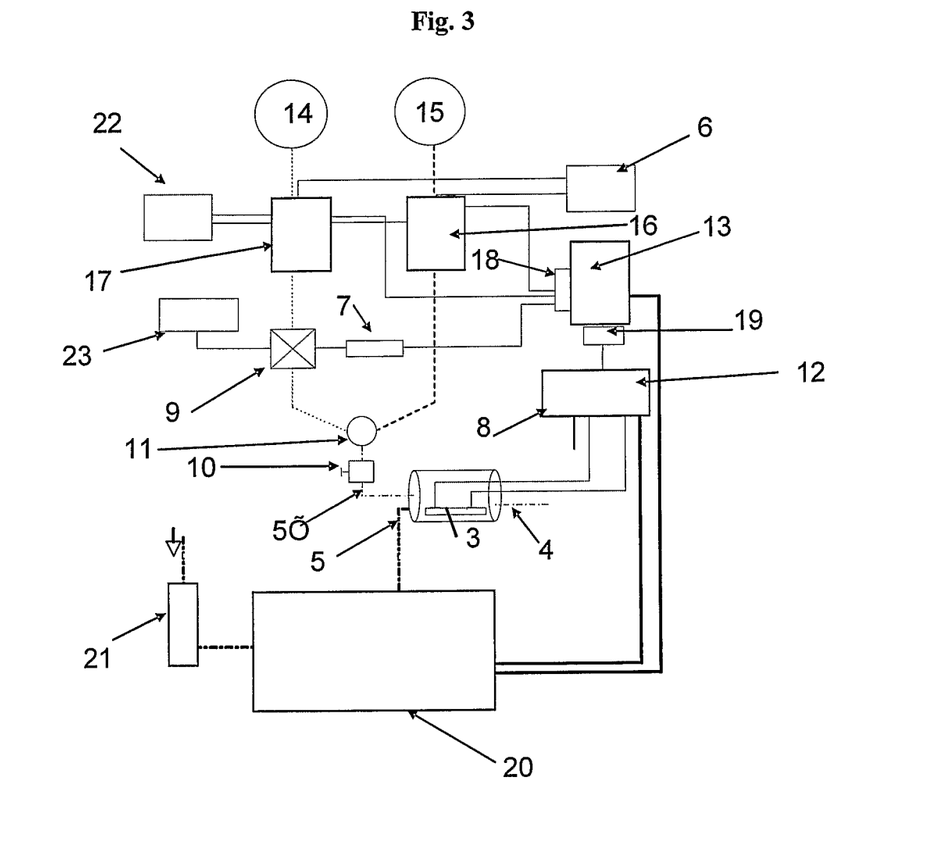
FIG. 3 shows a sensor for detecting electron-donor or electron-acceptor species that comprises a semiconductor transducer according to the invention.

A sensor for detecting electron-donor or electron-acceptor species that comprises a semiconductor transducer according to the invention is another subject of the present invention. One embodiment is shown in FIG. 3 in which the following may be distinguished: the sensitive element in its enclosure; the electronic part, which biases the devices, the data acquisition system and the gas circuit. The various constituents of the device are as follows:

3 detection cell containing the semiconductor transducer;
4 detection cell gas outlet;
5, 5' $NH_3$/Ar mixture or air/ozone mixture inlet into the detection cell;
6, 7 two voltage dividers;
8 thermocouple;
9 solenoid valve controlled by a time delay;
10 safety valve;
11 gas flow mixer;
12 electrometer;
13 computer;
14 $NH_3$ source;
15 Ar source;
16, 17 two gas flow regulators;
18 analog data acquisition device;
19 digital data acquisition device;
20 ozone analyzer/generator (0341M from Environment S.A.);
21 active carbon filter;
22 0-15 volt DC power supply;
23 −12/+12 volt DC power supply.

The lines have the following meaning:
——— electrical connections;
- - - - - gas transfer/purge (Ar, $N_2$)
·········· $NH_3$ transfer;

transfer of the gas to be analyzed ($NH_3$/Ar or air/ozone mixture) to the detection cell 3.

A sensor comprising a transducer according to the present invention is particularly useful for detecting gaseous species, especially for detecting electron-acceptor molecules such as $O_3$ or $NO_2$ or electron-donor molecules, such as $NH_3$.

When a sensor according to the invention is intended for detecting electron-acceptor (and/or oxidizing) molecules, the layer M1 of the transducer is preferably formed by a nonfluorinated non-radical metal monophthalocyanine MPc or by an oligothiophene, and the layer M2 is a lanthanide bisphthalocyanine, in particular $LuPc_2$. Copper monophthalocyanine CuPc and $\alpha,\omega$-dihexylsexithiophene give good performance.

When a sensor according to the invention is intended for detecting electron-donor (and/reducing) molecules, the layer M1 of the transducer is preferably formed by a perfluorinated non-radical metal monophthalocyanine or by a perylene diimide, and the layer M2 is a lanthanide bisphthalocyanine, in particular $LuPc_2$. The monophthalocyanine $CuF_{16}Pc$ and N,N-dipentyl-perylene tetracarboxylic acid diimide give good performance.

The use of a partially fluorinated monophthalocyanine depends on the structure of the entire transducer. When the electrodes are Au or ITO electrodes, a transducer according to the invention in which M1 is a compound of $M^{II}Pc$ in which the monophthalocyanine is partially fluorinated is effective for detecting electron-acceptor molecules.

Replacing a semiconductor transducer of the prior art, of diode, field-effect transistor or resistor type, with a transducer according to the present invention results in a sensor for detecting electron-donor or electron-acceptor species which performs substantially better through the presence of a particular heterojunction. The actual structure of the transducer makes it adaptable to various analytes and in particular allows selective detection, stable over time, at room temperature. The selectivity and the stability of the sensor in particular cases are obtained by an appropriate choice of the material forming the layer M1.

The present invention is described in greater detail by the following examples, it is however not limited thereto.

In these examples, the arrangement as shown in FIG. 3 described above was used for detecting gaseous species.

As material M1, phthalocyanines, 1'$\alpha,\omega$-dihexylsexithiophene ($\alpha,\omega$-dihexyl-6T) or N,N-dipentyl-perylene tetracarboxylic acid diimide (PTCDI) was used.

The phthalocyanines used were CuPc, $CuF_8Pc$, $CuF_{16}Pc$ and $Lu(Pc)_2$.

The monophthalocyanine $CuF_8Pc$ was prepared by reacting 4,5-difluoro-1,2-dibromobenzene (27.2 g; 0.1 mol) with copper cyanide CuCN (26.9 g; 0.3 mol) at 150° C. for 2 hours in 50 ml of DMF. The reaction mixture was treated twice with a concentrated ammonia solution and then filtered. The solid product thus recovered was washed with $CHCl_3$ in a Soxhlet and then vacuum-dried at 100° C. A fine blue powder with a yield of 80% was obtained [composition for $C_{32}H_8F_8N_8Cu$: calculated: 53.38% C; 1.12% H; 21.11% F; 8.83% Cu, measured: 52.74% C; 1.13% H; 21.03% F; 9.17% Cu.]

The bisphthalocyanine $Lu(Pc)_2$ was prepared by reacting lutecium triacetate with ortho-dicyanobenzene with no solvent at 300° C.

The CuPc, $CuF_{16}Pc$, $\alpha,\omega$-dihexyl-6T and PTCDI are products sold by the company Sigma-Aldrich.

Example 1

This example is aimed at showing the difference in behavior of transducers of the resistor type in the case of $CuF_8Pc$ or $Lu(Pc)_2$ and of the $Lu(Pc)_2$ on $CuF_8Pc$ heterojunction type.

Resistor Preparation

Platinum electrodes were deposited by screen printing on an alumina substrate, followed by a monophthalocyanine film. In the case of $CuF_8Pc$, a film having a thickness of 300 nm was obtained by vacuum sublimation. In the case of $LuPc_2$, a film having a thickness of 100 nm was obtained by solvent casting.

Heterojunction Preparation

Platinum electrodes were deposited on an alumina substrate by screen printing. Next, a $CuF_8Pc$ film with a thickness of 300 nm and then an $Lu(Pc)_2$ film with a thickness of 100 nm were deposited in succession by vacuum evaporation.

Each of these transducers was tested in a device as shown in FIG. 3 by alternately passing a flow of air containing no ozone and a flow of air containing about 700 ppb of ozone through it.

Figure 4A:
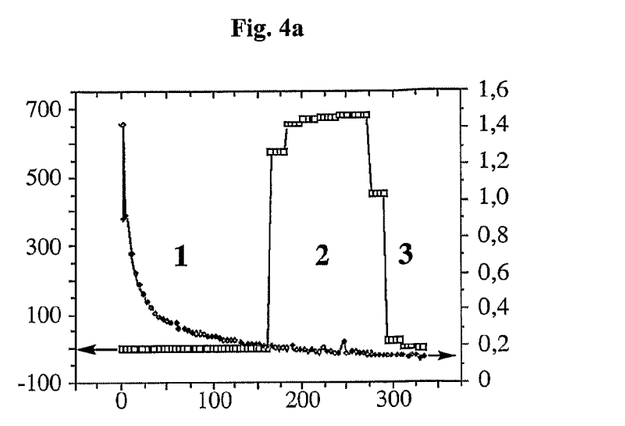
FIGS. 4a-4c show the variation in current I (in picoamps, plotted on the right-hand y-axis) as a function of time (in seconds, plotted on the x-axis) i.e. as a function of the instantaneous ozone content (in ppb, plotted on the left-hand y-axis) in the gas flow according to the invention.
Figure 4B:
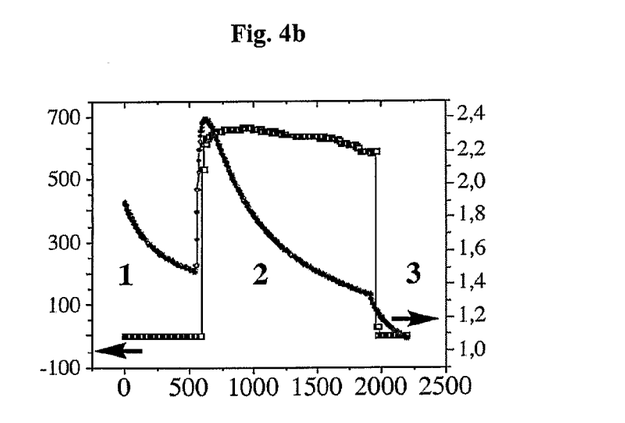
Figure 4C:
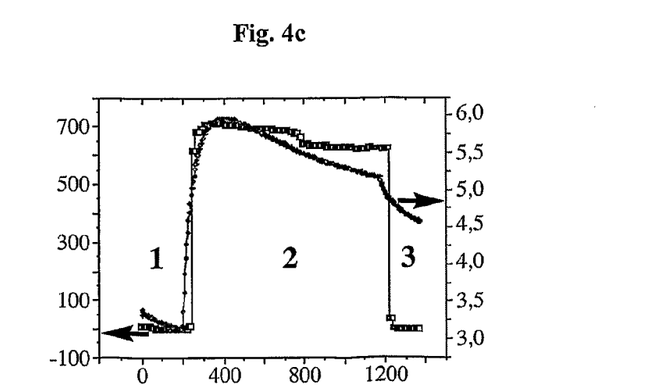

FIGS. 4a, 4b and 4c show the variation in current I (in picoamps, plotted on the right-hand y-axis) as a function of time (in seconds, plotted on the x-axis) i.e. as a function of the instantaneous ozone content (in ppb, plotted on the left-hand y-axis) in the gas flow. The regions 1 and 3 correspond to an air atmosphere containing no ozone and the region 2 corresponds to an atmosphere containing ozone. Each arrow indicates the scale to which the corresponding curve refers.

In each of the figures, the light gray curve shows the variation in the current and the black curve shows the variation in the gas composition. It is apparent that:
- the $CuF_8Pc$ resistor has a very low conductivity and does not react with ozone;
- the $Lu(Pc)_2$ resistor reacts very sharply with ozone, but the reaction is not stable over time;
- the $Lu(Pc)_2$ on $CuF_8Pc$ heterojunction has a much higher conductivity than just the $CuF_8Pc$ layer—it reacts significantly and the stability is considerably improved over that of an $Lu(Pc)_2$ resistor.

These results clearly show the surprising effect resulting from the use of a heterojunction in a transducer according to the invention compared with the resistor-type transducers of the prior art.

Examples 2

This example aims to show the difference in behavior of transducers of the $Lu(Pc)_2$ on $CuF_xPc$ heterojunction type, where x is 0, 8 or 16, depending on whether the transducer is exposed to a gas containing $O_3$ or to a gas containing $NH_3$.

Transducers Used for Detecting $O_3$

Au electrodes were deposited by vacuum sublimation on a silica-coated silicon substrate, said electrodes being separated by 10 µm. Next, a $CuF_xPc$ film was deposited by vacuum sublimation, followed by an $Lu(Pc)_2$ film, again by vacuum sublimation, the phthalocyanine films each having a thickness (controlled by a piezoelectric quartz microbalance) of 100 nm. For both phthalocyanine layers, the deposition was carried out using a VEECO 770 system under a pressure of $10^{-6}$ torr with a deposition rate of 2 Å/s.

Each of the transducers thus obtained was tested in an arrangement similar to that shown in FIG. 3, equipped with an ozone generator/analyzer, by making a flow of air containing 90 ppb ozone flow through it, followed by a flow of clean air (filtered on active carbon) containing no ozone, with a flow rate of 1.6 l/min.

Figure 5:
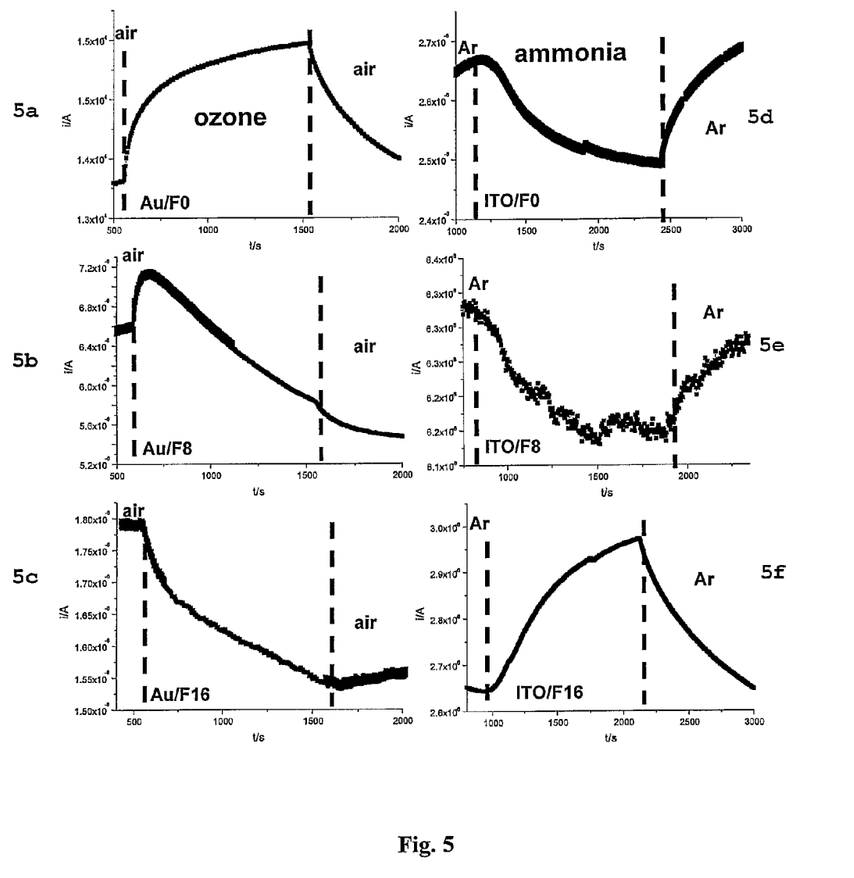
FIGS. 5a, 5b and 5c show the variation in current I (in amps) as a function of time (in seconds) for each of the transducers containing CuPc, $CuF_8Pc$ and $CuF_{16}Pc$ respectively according to the invention.
FIGS. 5d, 5e and 5f show the variation in current I (in amps) as a function of time (in seconds) for the transducers containing CuPc, $CuF_8Pc$ and $CuF_{16}Pc$ respectively according to the invention.

FIGS. 5a, 5b and 5c show the variation in current I (in amps) as a function of time (in seconds) for each of the transducers containing CuPc, $CuF_8Pc$ and $CuF_{16}Pc$ respectively.

These figures show the advantage of the transducer used, in particular the considerable influence of the material M1 on the response of the device. In particular, the current increases in the presence of ozone when M1 is CuPc and decreases when M1 is $CuF_{16}Pc$. CuPc gives the most stable response with respect to ozone, with good sensitivity.

Transducers Used for an $NH_3$ Detection

An ITO film forming electrodes was deposited on a glass substrate by sputtering. Said electrodes were separated by 75 μm. Next, a $CuF_xPc$ film and then an $Lu(Pc)_2$ film were deposited, under the same conditions as in the case of the transducer for $O_3$ detection, using a VEECO 770 system under a pressure of $10^{-6}$ torr with a deposition rate of 2 Å/s, each of the phthalocyanine films having a thickness of 100 nm.

Each of these transducers was tested in a device similar to that of FIG. 3, equipped with a mass flowmeter system for regulating the $NH_3$ flow, from $NH_3$ bottles and Ar flow, by passing a gas flow containing 35 ppm $NH_3$ and then a gas flow containing no $NH_3$ pass through it with a flow rate of 0.5 l/min.

FIGS. 5d, 5e and 5f show the variation in current I (in amps) as a function of time (in seconds) for the transducers containing CuPc, $CuF_8Pc$ and $CuF_{16}Pc$ respectively.

As previously, these figures show the advantage of the transducer used, in particular the considerable influence of the material M1 on the response of the device. In particular, the current increases in the presence of $NH_3$ when M1 is $CuF_{16}Pc$, and decreases when M1 is CuPc. These figures also show that the use of $CuF_{16}Pc$ as material M1 is favorable for detecting $NH_3$.

Examples 3

This example is aimed at illustrating a transducer of the $Lu(Pc)_2$ on α,ω-dihexyl-6T heterojunction type and the reversibility of the response obtained when it is used for detecting ozone.

Such a transducer was prepared according to the process described above in example 2 according to the procedure described for the preparation of transducers used for detecting ozone; each of the α,ω-dihexyl-6T and $Lu(Pc)_2$ films has a thickness of 100 nm.

This transducer was then tested in an arrangement similar to that shown in FIG. 3, equipped with an ozone generator/analyzer, by passing a flow of air containing 400 ppb ozone and then a flow of clean air (filtered on active carbon) containing no ozone, with a flow rate of 1.6 l/min, through it according to the following protocol:

three cycles: ozone flow for 5 min (exposure)/air flow for 15 min (rest); then three cycles: ozone flow for 2 min air flow for 8 min.

Figure 6A:
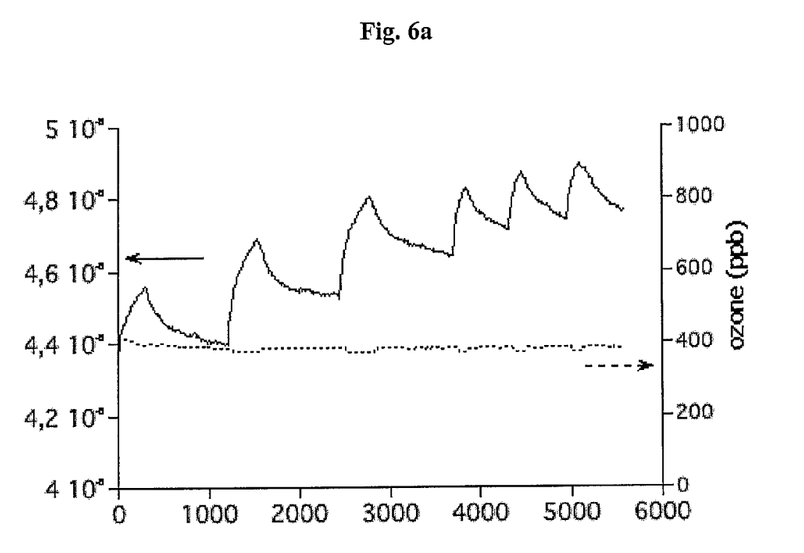
FIGS. 6a and 6b shows test results for a test of the transducer in an arrangement similar to that shown in FIG. 3 according to the invention.
Figure 6B:
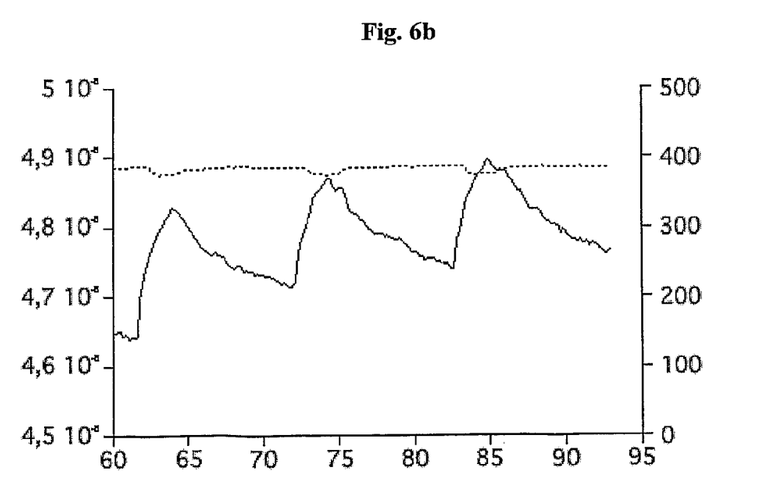

The results obtained are given in appended FIGS. 6a and 6b which show:

FIG. 6a: the variation in current I (in nA on the left-hand y-axis) as a function of time (in seconds on the x-axis), i.e. as a function of the instantaneous ozone content (in ppb, on the right-hand y-axis) in the gas flow. Each arrow indicates the scale to which the corresponding curve refers (solid curve: intensity of the current; dotted curve: instantaneous ozone content); and FIG. 6b: the variation in current I (in nA on the left-hand y-axis) as a function of time (in minutes on the x-axis), i.e. as a function of the instantaneous ozone content (in ppb, on the right-axis) in the gas flow.

The curve of FIG. 6a shows that irrespective of the operating method used, the response is reproducible, better reversibility of the sensor being obtained however with the shortest cycles (2 min exposure/8 min rest). The curve of FIG. 6b shows only the results obtained for the short cycles.

Example 4

This example is aimed at illustrating a transducer of the $Lu(Pc)_2$ on PTCDI heterojunction type and the reversibility of the response obtained when it is used for detecting ammonia.

Such a transducer was prepared according to the process described above in example 2 according to the procedure described for preparing the transducers used for detecting ammonia; each of the PTDCI and $Lu(Pc)_2$ films has a thickness of 100 nm.

This transducer was then tested in an arrangement similar to that shown in FIG. 3, equipped with a mass flowmeter system for regulating the $NH_3$ flow from $NH_3$ bottles and Ar flow, passing an $NH_3$/Ar gas flow containing 1000 ppm of $NH_3$ and then a gas flow containing no $NH_3$ pass through it with a flow rate of 0.5 l/min according to the following protocol:

three cycles: $NH_3$/Ar flow for 5 min (exposure)/flow with no $NH_3$ for 15 min (rest), then three cycles: $NH_3$/Ar flow for 2 min/flow with no $NH_3$ for 8 min.

Figure 7:
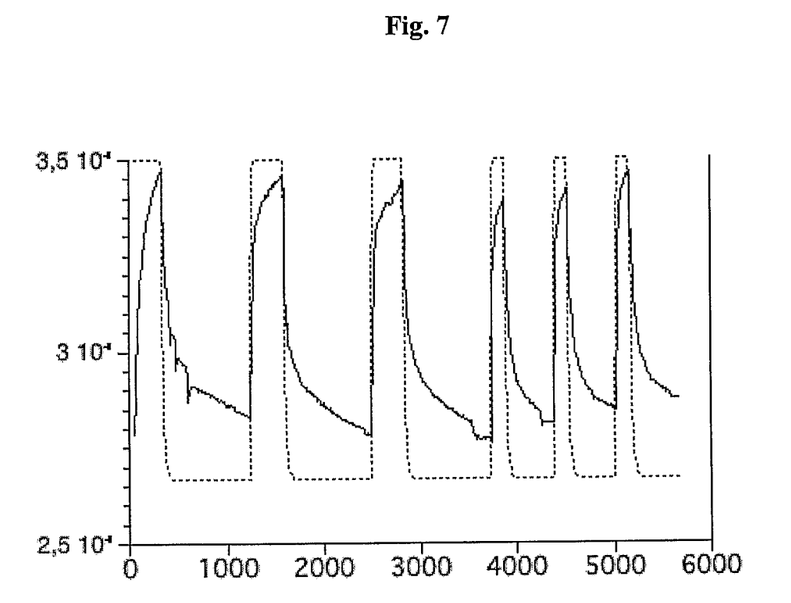
FIG. 7 shows the variation in current I (in A on the y-axis) as a function of time (in seconds on the x-axis) and corresponds to the solid curve.

The results obtained are given in appended FIG. 7, which shows the variation in current I (in A on the y-axis) as a function of time (in seconds on the x-axis) and corresponds to the solid curve. The dotted curve corresponds to the $NH_3$/Ar exposure/rest cycles.

The sensor shows very good reversibility whatever the duration of the $NH_3$/Ar exposure/rest cycles.

The invention claimed is:

1. A transducer comprising:
an insulating substrate; and
two electrodes and a semiconductor sensitive element deposited on said insulating substrate wherein,
the sensitive element is formed by a layer of a semiconductor molecular material M1 which has a conductivity $C_1$ and a layer of a semiconductor molecular material M2 which has a conductivity $C_2$ and a bandgap $E_{g2} < 1$ eV;
the layer of material M1 is in contact with the electrodes;
the layer of material M2 is deposited on the layer of material M1 and is not in contact with the electrodes;
the conductivities are such that $C_2/C_1 \geq 1$; and
the material M1 is: a monophthalocyanine $M^{II}Pc$ of a metal M in oxidation state II chosen from Fe, Co, Ni, Cu, Zn, Pt and Pd; a monophthalocyanine $M^{III}Pc$ of a metal M in oxidation state III in the form GaOH, GaCl, InCl, AlCl, AlF or AlOH; a monophthalocyanine $M^{IV}Pc$ of a metal M in oxidation state IV in the form $Si(OH)_2$, $SiCl_2$, $SnCl_2$, TiO or VO; a polyphthalocyanine, the repeat unit of which is MPc, the metal M being in the form SiO, SnO, GeO, FePyrazine, RuPyrazine, AlF or GaF; an organic compound chosen from oligothiophenes, whether substituted or not, tetracenes, pentacenes, fullerenes, tetracarboxylic naphthalenes, naphthalene dianhydrides, naphthalene diimides, tetracarboxylic perylenes, perylene dianhydrides, perylene diimides, triarylamines, triphenylenes and tetracyanoquinodimethanes; or a semiconductor polymer chosen from polythiophenes and polyparaphenylenevinylenes.

2. The transducer as claimed in claim 1, wherein the thickness of each of the layers of M1, M2 and the electrodes is between 2 and 1000 nm.

3. The transducer as claimed in claim 1, wherein the material M2 is chosen from the group consisting of:
- metal bisphthalocyanines (M'Pc$_2$), metal bisporphyrins (M'Por$_2$), metal bisnaphthalocyanines (M'Nc$_2$) and metal derivatives,
  - said metal derivatives selected from the group consisting of a tetrapyrazinoporphyrazine, thiophenoporphyrazine, a tetraarenoporphyrazine, a tetrapyridoporphyrazine, an anthracocyanine, a triphenylocyanine and a phenanthrocyanine,
- where among said group M' is any one of U, Zr, Y and Ln
  - where Ln is selected from the group consisting of (La, Ce, Pr, Nd, Sm, Eu, Gd, Tb, Dy, Ho, Er, Tm, Yb and Lu; and
- metal trisphthalocyanines (M'$_2$Pc$_3$), metal trisporphyrins (M'$_2$Por$_3$), metal trisnaphthalocyanines (M'$_2$Nc$_3$) and metal derivatives
  - said metal derivatives selected from the group consisting of a tetrapyrazinoporphyrazine, a thiophenoporphyrazine, a tetraarenoporphyrazine, a tetrapyridoporphyrazine, an anthracocyanine, a triphenylocyanine and a phenanthrocyanine,
- where among said group M' is either one of Y and Ln.

4. The transducer as claimed in claim 1, wherein M1 is a monophthalocyanine bearing halogens.

5. The transducer as claimed in claim 4, wherein the material M1 is a tetrafluorinated, octafluorinated or perfluorinated monophthalocyanine.

6. The transducer as claimed in claim 1, wherein the insulating substrate bearing the electrodes, the layer of material M1 and the layer of material M2, is formed by an intrinsic insulating material or by a material coated with dielectric.

7. The transducer as claimed in claim 6, wherein said intrinsic insulating material is alumina or glass.

8. The transducer as claimed in claim 6, wherein the material coated with a dielectric is formed by silicon coated with a film of silica or silicon nitride.

9. The transducer as claimed in claim 1, wherein the electrodes are formed by a film of gold or by a film of indium tin oxide (ITO).

10. The transducer as claimed in claim 9, wherein the electrodes are in the form of interdigitated electrodes.

11. A sensor for detecting gaseous electron-acceptor or electron-donor species, wherein said sensor has a transducer as claimed in claim 1.

12. The sensor as claimed in claim 11, for detecting electron-acceptor molecules, wherein the material M1 of the transducer is a nonfluorinated non-radical metal monophthalocyanine or an oligothiophene, and the layer M2 is a lanthanide bisphthalocyanine.

13. The sensor as claimed in claim 12, wherein the material M1 is a copper monophthalocyanine and the material M2 is a lutetium bisphthalocyanine.

14. The sensor as claimed in claim 11, for detecting electron-donor molecules, wherein the material M1 of the transducer is a perfluorinated non-radical metal monophthalocyanine or a perylene diimide, and the material M2 is a lanthanide bisphthalocyanine.

15. The sensor as claimed in claim 14, wherein the material M1 is a perfluorinated copper monophthalocyanine and the material M2 is a lutetium bisphthalocyanine.

16. The sensor as claimed in claim 14, wherein the material M1 is a partially fluorinated metal monophthalocyanine, the material M2 is a lutetium bisphthalocyanine and the electrodes are made of ITO or Au.

* * * * *